United States Patent
Ida

(10) Patent No.: US 9,410,842 B2
(45) Date of Patent: Aug. 9, 2016

(54) PHOTOACOUSTIC WAVE MEASUREMENT DEVICE

(71) Applicant: ADVANTEST CORPORATION, Tokyo (JP)

(72) Inventor: Taiichiro Ida, Gunma (JP)

(73) Assignee: ADVANTEST CORPORATION, Tokyo (JP)

( * ) Notice: Subject to any disclaimer, the term of this patent is extended or adjusted under 35 U.S.C. 154(b) by 0 days.

(21) Appl. No.: 14/397,939

(22) PCT Filed: Jul. 19, 2013

(86) PCT No.: PCT/JP2013/070263
§ 371 (c)(1),
(2) Date: Oct. 30, 2014

(87) PCT Pub. No.: WO2014/030491
PCT Pub. Date: Feb. 27, 2014

(65) Prior Publication Data
US 2015/0122036 A1    May 7, 2015

(30) Foreign Application Priority Data

Aug. 20, 2012 (JP) ................................. 2012-181435

(51) Int. Cl.
*G01D 5/32* (2006.01)
*G01H 9/00* (2006.01)
(Continued)

(52) U.S. Cl.
CPC ............... *G01H 9/00* (2013.01); *A61B 5/0095* (2013.01); *G01H 9/004* (2013.01); *G01N 21/1702* (2013.01); *G01N 29/2418* (2013.01)

(58) Field of Classification Search
CPC ..... G01H 9/00; G01H 9/004; G01H 29/2418; G01H 21/1702; A61B 5/0095
See application file for complete search history.

(56) References Cited

U.S. PATENT DOCUMENTS

| 4,543,486 A | * | 9/1985 | Rose | ...................... B23K 26/03 |
| | | | | 219/121.14 |
| 5,125,749 A | | 6/1992 | Leugers et al. | |

(Continued)

FOREIGN PATENT DOCUMENTS

| JP | 4-264236 | 9/1992 |
| JP | 10-197496 | 7/1998 |

(Continued)

OTHER PUBLICATIONS

Taiichiro Ida et al., "Real Time Hikari Onkyo Imaging-ho ni yoru Nessho Shindan", Diagnose of Burns by real time photoacoustic imaging, Journal of Medical Ultrasonics, vol. 39, Supplement, the Japan Society of Ultrasonics in Medicine, Apr. 15, 2012, pp. S489.

(Continued)

*Primary Examiner* — Harshad R Patel
*Assistant Examiner* — Samir M Shah
(74) *Attorney, Agent, or Firm* — Greenblum & Bernstein P.L.C.

(57) ABSTRACT

A photoacoustic wave measurement device according to the present invention includes: an optical fiber that outputs pulsed light; an external spacer that is disposed between a pulsed-light output end of the optical fiber and a measurement object, and which is adapted to allow the pulsed light to pass therethrough; a piezoelectric element that receives a photoacoustic wave generated by the pulsed light from the measurement object and converts the photoacoustic wave into an electric signal; and a spacer that is disposed between the external spacer and the piezoelectric element, and which is adapted to allow the photoacoustic wave to pass therethrough. The piezoelectric element is farther from the measurement object than the pulsed-light output end. A part of the optical fiber is disposed within the spacer.

6 Claims, 3 Drawing Sheets

(51) Int. Cl.
*A61B 5/00* (2006.01)
*G01N 29/24* (2006.01)
*G01N 21/17* (2006.01)

(56) References Cited

U.S. PATENT DOCUMENTS

| | | | |
|---|---|---|---|
| 8,864,667 B2* | 10/2014 | Asao | A61B 5/742 600/437 |
| 2005/0070803 A1* | 3/2005 | Cullum | A61B 5/0095 600/473 |
| 2006/0264717 A1 | 11/2006 | Pesach et al. | |
| 2007/0015978 A1 | 1/2007 | Kanayama et al. | |
| 2010/0191109 A1* | 7/2010 | Fukutani | A61B 5/0059 600/437 |
| 2011/0112391 A1* | 5/2011 | Nishihara | A61B 5/0059 600/407 |
| 2011/0275890 A1* | 11/2011 | Wang | A61B 5/0062 600/104 |
| 2012/0179041 A1* | 7/2012 | Nakagawa | A61B 5/0073 600/443 |
| 2012/0190963 A1* | 7/2012 | Fukutani | A61B 5/0091 600/407 |
| 2012/0325006 A1 | 12/2012 | Suzuki | |
| 2013/0006090 A1* | 1/2013 | Miyasato | A61B 5/0091 600/407 |
| 2013/0031982 A1* | 2/2013 | Sato | A61B 8/08 73/655 |
| 2013/0039147 A1* | 2/2013 | Witte | A61B 5/0093 367/7 |
| 2013/0114859 A1* | 5/2013 | Wanda | A61B 5/0095 382/103 |
| 2014/0018659 A1* | 1/2014 | Fukutani | A61B 5/0095 600/407 |
| 2014/0118749 A1* | 5/2014 | Nakajima | G01N 21/1702 356/519 |
| 2014/0309515 A1 | 10/2014 | Ida | |
| 2014/0309516 A1 | 10/2014 | Ida | |
| 2014/3072259 | 10/2014 | Ida | |

FOREIGN PATENT DOCUMENTS

| | | |
|---|---|---|
| JP | 2004-351023 | 12/2004 |
| JP | 2006-516207 | 6/2006 |
| JP | 2010-125260 A | 6/2010 |
| JP | 2011-143259 | 7/2011 |
| JP | 2011-229660 | 11/2011 |
| WO | 2010/005109 | 1/2010 |

OTHER PUBLICATIONS

Search report from International Patent Appl. No. PCT/JP2013/070263, mail date is Oct. 15, 2013.

Zuomin Zhao et al., "Backward-mode photoacoustic transducer for sensing optical scattering and ultrasonic attenuation: determing fraction consistencies in pulp suspensions.", Measurement Science and Technology, IOP, Bristol, GB, vol. 21, No. 2, Feb. 1, 2010, pp. 25105 (8pp).

European Search Report, mailed Dec. 23, 2015, with respect to European Patent Application No. 13830910.9.

\* cited by examiner

Comparative Example

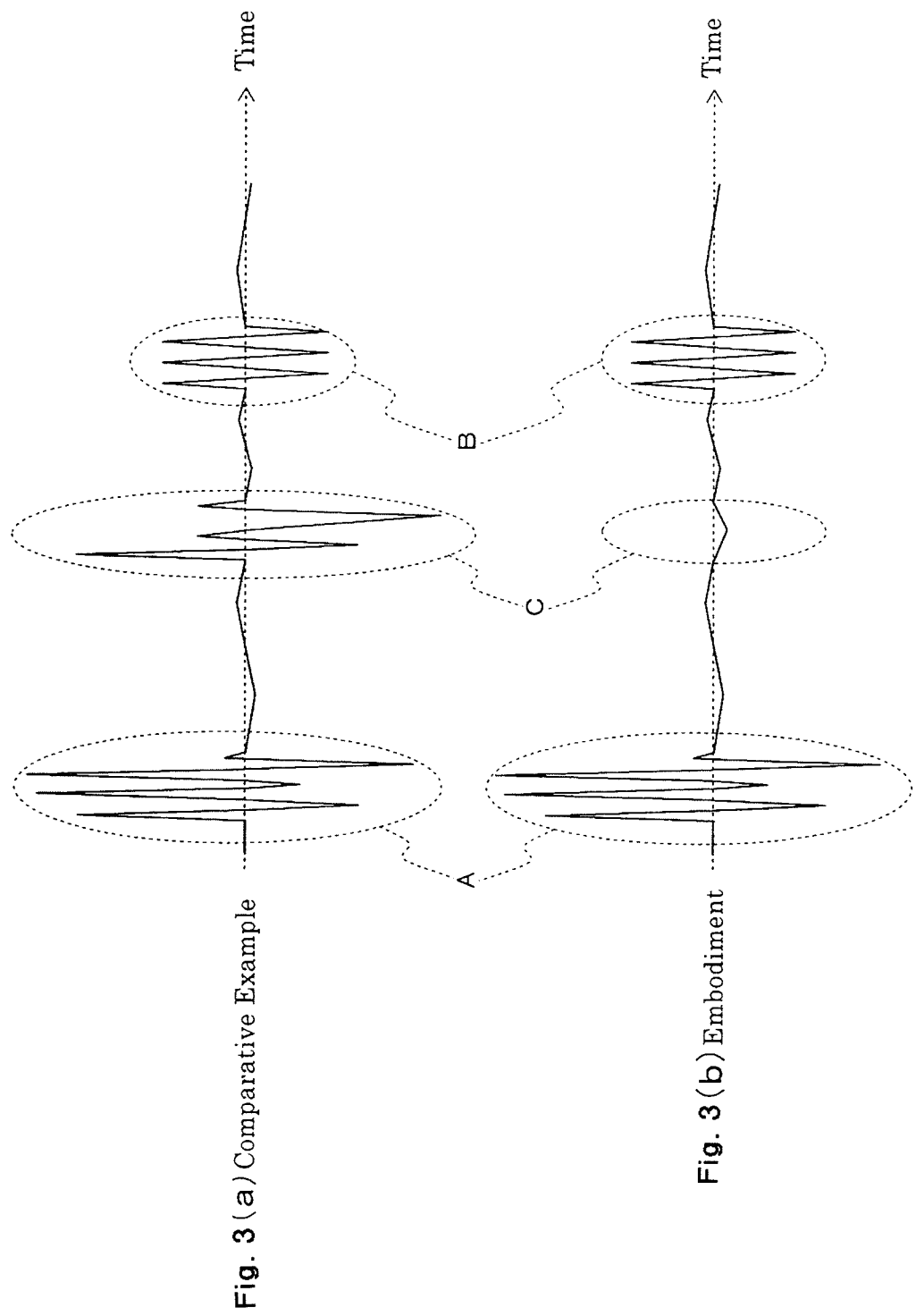

PHOTOACOUSTIC WAVE MEASUREMENT DEVICE

FIELD OF THE INVENTION

The present invention relates to photoacoustic sensors.

BACKGROUND ART

Photoacoustic sensors are conventionally known to measure a photoacoustic signal generated by irradiating an object to be measured (for example, biological object) with pulsed light (see, for example, Patent Document 1 (Japanese Unexamined Patent Publication No. 2011-229660)).

SUMMARY OF THE INVENTION

However, the photoacoustic signal obtained by the photoacoustic sensor may include noise.

Accordingly, it is an object of the present invention to reduce noise included in a photoacoustic signal obtained by a photoacoustic wave measurement device.

According to the present invention, a photoacoustic wave measurement device, includes: a light outputting portion that outputs light therefrom; an arrangement member that is disposed between a light output end of the light outputting portion and a measurement object, and which is adapted to allow the light to pass therethrough; a photoacoustic wave detector that receives a photoacoustic wave generated by the light from the measurement object and converts the photoacoustic wave into an electric signal; and a photoacoustic wave transmission member that is disposed between the arrangement member and the photoacoustic wave detector, and which is adapted to allow the photoacoustic wave to pass therethrough, wherein the photoacoustic wave detector is farther from the measurement object than the light output end, and a part of the light outputting portion is disposed within the photoacoustic wave transmission member.

According to the thus constructed photoacoustic wave measurement device, a light outputting portion outputs light therefrom. An arrangement member is disposed between a light output end of the light outputting portion and a measurement object, and is adapted to allow the light to pass therethrough. A photoacoustic wave detector receives a photoacoustic wave generated by the light from the measurement object and converts the photoacoustic wave into an electric signal. A photoacoustic wave transmission member is disposed between the arrangement member and the photoacoustic wave detector, and is adapted to allow the photoacoustic wave to pass therethrough. The photoacoustic wave detector is farther from the measurement object than the light output end. A part of the light outputting portion is disposed within the photoacoustic wave transmission member.

According to the photoacoustic wave measurement device of the present invention, the light outputting portion may penetrate the photoacoustic wave transmission member.

According to the photoacoustic wave measurement device of the present invention, the light outputting portion may be an optical fiber.

According to the photoacoustic wave measurement device of the present invention, the photoacoustic wave detector may be a piezoelectric element.

BRIEF DESCRIPTION OF DRAWINGS

FIGS. 3(a) and 3(b) show conceptually graphs of a waveform detected by the photoacoustic wave measurement device 1 (see FIG. 2) in the comparative example (see FIG. 3(a)), as well as a waveform detected by the photoacoustic wave measurement device 1 (see FIG. 1) in the embodiment of the present invention (see FIG. 3(b)).

DETAILED DESCRIPTION OF THE DISCLOSURE

In the following, preferred embodiment of the present invention will be described with reference to the accompanying drawings.

Figure 1:
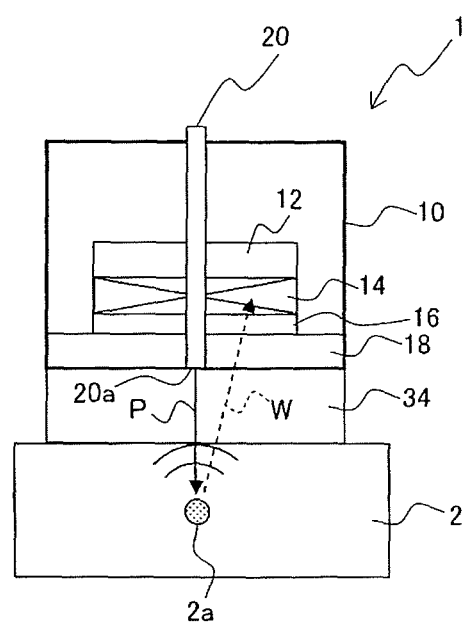
FIG. 1 is a cross-sectional view of a photoacoustic wave measurement device 1 according to an embodiment of the present invention.

FIG. 1 is a cross-sectional view of a photoacoustic wave measurement device 1 according to an embodiment of the present invention. The photoacoustic wave measurement device 1 includes a case 10, a backing member 12, a piezoelectric element (photoacoustic wave detector) 14, an electrode 16, a spacer (photoacoustic wave transmission member) 18, an optical fiber (light outputting portion) 20, and an external spacer (arrangement member) 34.

The case 10 is a case for accommodating therein the backing member 12, the piezoelectric element 14, the electrode 16, and the spacer 18. The spacer 18 is in contact with the bottom surface of the case 10, and the electrode 16 is mounted on the spacer 18. The piezoelectric element 14 is mounted on the electrode 16, and the backing member 12 is mounted on the piezoelectric element 14.

The backing member 12 serves as a backing material made of epoxy resin. The piezoelectric element (photoacoustic wave detector) 14 receives a pressure caused by compression waves or the like and converts the pressure into voltage. The electrode 16 receives the voltage from the piezoelectric element 14 and supplies the voltage to an external measurement device, not shown (for example, an oscilloscope). The electrode 16 is, for example, a gold electrode.

The spacer (photoacoustic wave transmission member) 18 is a transparent spacer that allows a compression wave (photoacoustic wave W) to pass therethrough, and which is made of, for example, acryl, epoxy, a fused quartz, or the like. The spacer 18 is disposed between the arrangement member 34 and the piezoelectric element (photoacoustic wave detector) 14. The spacer 18 is separately formed from the arrangement member 34. Note that the spacer 18 allows light and the photoacoustic wave to pass therethrough, and serves as a matching layer that matches an acoustic impedance of a measurement object 2 to that of the piezoelectric element 14.

The optical fiber (light outputting portion) 20 outputs light (for example, pulsed light P) from a pulsed-light output end 20a. The optical fiber 20 is connected to a pulsed light source (not shown) outside the photoacoustic wave measurement device 1.

The optical fiber 20 penetrates the case 10, the backing member 12, the piezoelectric element 14, and the electrode 16. Further, a part of the optical fiber 20 is disposed within the spacer (photoacoustic wave transmission member) 18. As shown in FIG. 1, the optical fiber 20 may penetrate the spacer 18.

The external spacer (arrangement member) 34 is disposed between the pulsed-light output end 20a and the measurement object 2 so as to allow the pulsed light P to pass therethrough. The external spacer 34 is in contact with the case 10 and the pulsed-light output end 20a, and also in contact with the measurement object 2. The external spacer 34 is a transparent spacer made of, for example, acryl, epoxy, a fused quartz, or the like.

The measurement object 2 is, for example, a ball of a finger of a human body. The measurement object 2 includes blood 2a in a blood vessel. When receiving the pulsed light P, the blood 2a in the blood vessel generates a photoacoustic wave W. The piezoelectric element 14 receives the photoacoustic wave W and converts the wave W into an electric signal (for example, in the form of voltage). The piezoelectric element 14 is farther from the measurement object 2 than the pulsed-light output end 20a.

Next, the operation of the one embodiment in the present invention will be described by comparing with a comparative example.

First, the pulsed light P emitted from the external pulsed light source (not shown) passes through the optical fiber 20, and then is output from the pulsed-light output end 20a. The pulsed light P is applied to the measurement object 2 through the external spacer 34.

The pulsed light P reaches the blood 2a in the blood vessel of the measurement object 2. Then, the blood 2a in the blood vessel absorbs the pulsed light P and is warmed and is then adiabatically expanded. Thus, the compression wave (photoacoustic wave W) is output from the blood 2a in the blood vessel.

The photoacoustic wave W reaches the piezoelectric element 14 through the measurement object 2, the external spacer 34, the spacer 18, and the electrode 16. The piezoelectric element 14 converts the pressure produced by the photoacoustic wave W into an electric signal (for example, in the form of a voltage). The voltage is taken out to the outside via the electrode 16, and then fed to the oscilloscope or the like.

Figure 2:
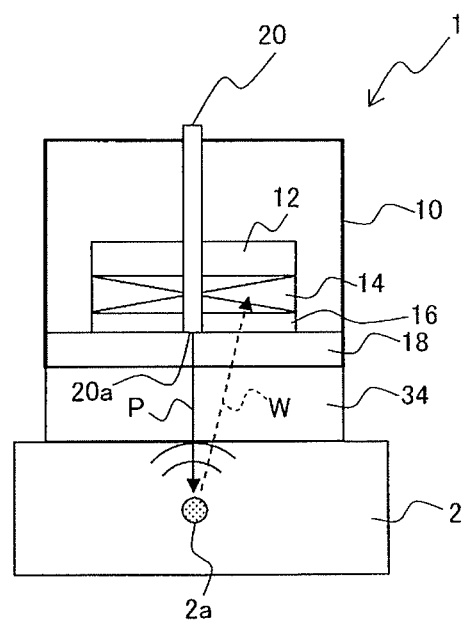
FIG. 2 is a cross-sectional view of another photoacoustic wave measurement device 1 according to a comparative example.

FIG. 2 is a cross-sectional view of another photoacoustic wave measurement device 1 according to a comparative example.

In the comparative example, in the photoacoustic wave measurement device 1 shown in FIG. 2, the optical fiber 20 is not inserted into the spacer 18 at all. In the comparative example, the pulsed-light output end 20a is in contact with the spacer 18.

FIGS. 3(a) and 3(b) show conceptually graphs of a waveform detected by the photoacoustic wave measurement device 1 (see FIG. 2) in the comparative example (see FIG. 3(a)), as well as a waveform detected by the photoacoustic wave measurement device 1 (see FIG. 1) in the embodiment of the present invention (see FIG. 3(b)).

The comparative example (see FIG. 3(a)) and the embodiment of the present invention (see FIG. 3(b)) do not differ so much in near-end reflection noise A generated directly after the pulsed light P starts to be output from the pulsed-light output end 20a.

In contrast, noise C generated between the near-end reflection noise A and a target signal B to be measured is large in the comparative example (see FIG. 3(a)), but small in the embodiment of the present invention (see FIG. 3(b)). This is the effect obtained by inserting the optical fiber 20 into the spacer 18 (particularly, by causing the optical fiber to penetrate the spacer).

In the comparative example (see FIG. 2), the pulsed-light output end 20a is located so close to the piezoelectric element 14 and the electrode 16 that the photoacoustic wave (noise C) generated in the vicinity of the pulsed-light output end 20a and reaching the piezoelectric element 14 becomes large. In contrast, in the embodiment of the present invention (see FIG. 1), the pulsed-light output end 20a is located so far from the piezoelectric element 14 and the electrode 16 that the photoacoustic wave (noise C) generated in the vicinity of the pulsed-light output end 20a and reaching the piezoelectric element 14 becomes small.

In the photoacoustic wave measurement device 1 of the embodiment of the present invention, the optical fiber 20 is inserted into (particularly, penetrates) the spacer 18, which can reduce noise included in the photoacoustic signal obtained by the photoacoustic wave measurement device 1.

Although the spacer 18 is a separate member from the arrangement member 34 as mentioned above, the spacer 18 and the arrangement member 34 may be integrally formed together.

The invention claimed is:

1. A photoacoustic wave measurement device, comprising:
   a light outputting portion that outputs light therefrom;
   an arrangement member that is disposed between a light output end of the light outputting portion and a measurement object, and which is configured to allow the light to pass therethrough;
   a photoacoustic wave detector that receives a photoacoustic wave that is generated by the light from the measurement object that is transmitted through the arrangement member, and converts the photoacoustic wave into an electric signal; and
   a photoacoustic wave transmission member that is disposed between the arrangement member and the photoacoustic wave detector, and which is configured to allow the photoacoustic wave to pass therethrough, wherein
   the photoacoustic wave detector is farther from the measurement object than the light output end, and
   a part of the light outputting portion is disposed within the photoacoustic wave transmission member.

2. The photoacoustic wave measurement device according to claim 1, wherein
   the light outputting portion penetrates the photoacoustic wave transmission member.

3. The photoacoustic wave measurement device according to claim 2, wherein the light outputting portion is an optical fiber.

4. The photoacoustic wave measurement device according to claim 2, wherein the photoacoustic wave detector is a piezoelectric element.

5. The photoacoustic wave measurement device according to claim 1, wherein the light outputting portion is an optical fiber.

6. The photoacoustic wave measurement device according to claim 1, wherein the photoacoustic wave detector is a piezoelectric element.

* * * * *